US00PP36431P3

(12) United States Plant Patent
Brazelton et al.

(10) Patent No.: US PP36,431 P3
(45) Date of Patent: Feb. 11, 2025

(54) BLUEBERRY PLANT NAMED 'FC13-113'

(50) Latin Name: *Vaccinium corymbosum*
Varietal Denomination: FC13-113

(71) Applicant: Fall Creek Farm and Nursery, Inc., Lowell, OR (US)

(72) Inventors: David M. Brazelton, Walterville, OR (US); Peter Stefan Boches, Hilo, HI (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 0 days.

(21) Appl. No.: 18/421,345

(22) Filed: Jan. 24, 2024

(65) Prior Publication Data

US 2024/0251689 P1 Jul. 25, 2024

Related U.S. Application Data

(60) Provisional application No. 63/440,983, filed on Jan. 25, 2023.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 5/08
See application file for complete search history.

(56) References Cited

U.S. PATENT DOCUMENTS

| | | | |
|---|---|---|---|
| PP15,146 | P3 | 9/2004 | Hancock |
| PP15,185 | P3 | 9/2004 | Hancock |
| PP25,386 | P3 | 3/2015 | Brazelton et al. |

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

The new blueberry plant 'FC13-113' is provided. 'FC13-113' is a commercial variety intended for the hand harvest fresh fruit market. The variety is produced from a cross of 'ZF06-231' (female parent, unpatented) and 'ZF08-189' (male parent, unpatented), which can be distinguished by its very large, high-quality fruit in the late season. Compared to other high chill varieties in this ripening window known to the Inventors, the fruit is much larger. The berry is very oblate with a distinct wide calyx. The plant is upright with medium vigor and high productivity.

7 Drawing Sheets

Latin name of the genus and species:
Genus—*Vaccinium.*
Species—*corymbosum.*
Variety denomination: The new blueberry plant claimed is of the variety denominated 'FC13-113'.

STATEMENT REGARDING FEDERALLY-SPONSORED RESEARCH AND DEVELOPMENT

None.

STATEMENT REGARDING PRIOR DISCLOSURES BY THE INVENTOR

The first sale of the new variety was Oct. 6, 2023, in the United States. The first sale of the new variety was by the inventor(s) or another who obtained the new variety directly or indirectly from the inventor(s). No plants of the new variety have been sold or offered for sale in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The present invention relates to the discovery of a new and distinct cultivar of northern highbush blueberry (*Vaccinium corymbosum*) plant, referred to as 'FC13-113', as herein described and illustrated.

Pedigree and History: The new blueberry plant originated from a cross of 'ZF06-231' (female parent, unpatented) and 'ZF08-189' (male parent, unpatented) made in Lowell, Oregon, U.S.A. in 2009. The seeds resulting from the above cross were sown and small plants were obtained which were physically and biologically different from each other. Selective study in 2013 in Lowell, Oregon, U.S.A. resulted in the identification of a single plant of the new variety. 'FC13-113' was selected in 2013 because, the fruit is much larger while maintaining increased firmness and flavor compared to other high chill varieties in the same ripening window known to the Inventors.

The new blueberry variety 'FC13-113' was initially propagated by softwood cuttings in 2013 from the original seedling in Lowell, Oregon, U.S.A. and planted in a replicated plot of nine plants in fall 2014. Additional replicated plots were established in Washington, U.S.A. and North Carolina, U.S.A. in 2018. The plants established in Oregon were successfully used to establish in vitro culture lines in 2017 and plants derived from the in vitro cultures were used to establish additional replicated plots for observation and yield data collection in Oregon, U.S.A., Washington, U.S.A., and other locations from 2018-2022.

Thus, 'FC13-113' has been found to undergo asexual propagation by soft wood cuttings and in vitro cultures in Oregon. Asexual propagation techniques in Oregon, such as soft wood cuttings and in vitro cultures, have shown that the characteristics of the new variety are homogenous, stable, and strictly transmissible by such asexual propagation from one generation to another. Accordingly, the new variety undergoes asexual propagation in a true-to-type manner with all the characteristics, as herein described, firmly fixed and retained through successive generations of such asexual reproduction.

SUMMARY OF THE INVENTION

The new blueberry plant 'FC13-113' is a commercial variety intended for the hand harvest fresh fruit market. The variety is distinguished by its very large, high-quality fruit in the late season. Compared to other high chill varieties in this ripening window known to the Inventors, the fruit is much larger while still maintaining high firmness and without sacrificing sweet aromatic flavor. The berry is very oblate with a distinct wide calyx. The plant is upright with medium vigor and high productivity.

The following characteristics of the new cultivar have been repeatedly observed and are determined to be the unique characteristics of the new blueberry plant 'FC13-113':

1) Very large berry size,
2) Oblate berry shape with a distinct wide calyx,
3) Sweet, highly aromatic flavor, and
4) High productivity.

The new variety of the present invention can readily be distinguished from its ancestors. More specifically, 'FC13-113' has a later ripening window compared to 'ZF06-231' (i.e., the female parent). In addition, 'FC13-113' has improved plant vigor and productivity compared to 'ZF08-189' (i.e., the male parent). 'ZF06-231' is a mid-late season selection with large, firm fruit and thick skin. 'ZF08-189' is a late season selection with low vigor and productivity. Moreover, the new variety can be readily distinguished from other similar non-parental varieties. For example, 'Last Call' (U.S. Plant Pat. No. 25,386) produces berries that have a smaller diameter compared to berries produced by the new variety.

BRIEF DESCRIPTION OF THE DRAWINGS

The accompanying photographic illustrations show typical specimens in full color of the foliage and fruit of the new variety 'FC13-113', which were two to seven years in age. The colors are as nearly true as is reasonably possible in a color representation of this type. The color values cited in the detailed botanical description accurately describe the colors of the new blueberry.

DETAILED BOTANICAL DESCRIPTION

Figure 1:
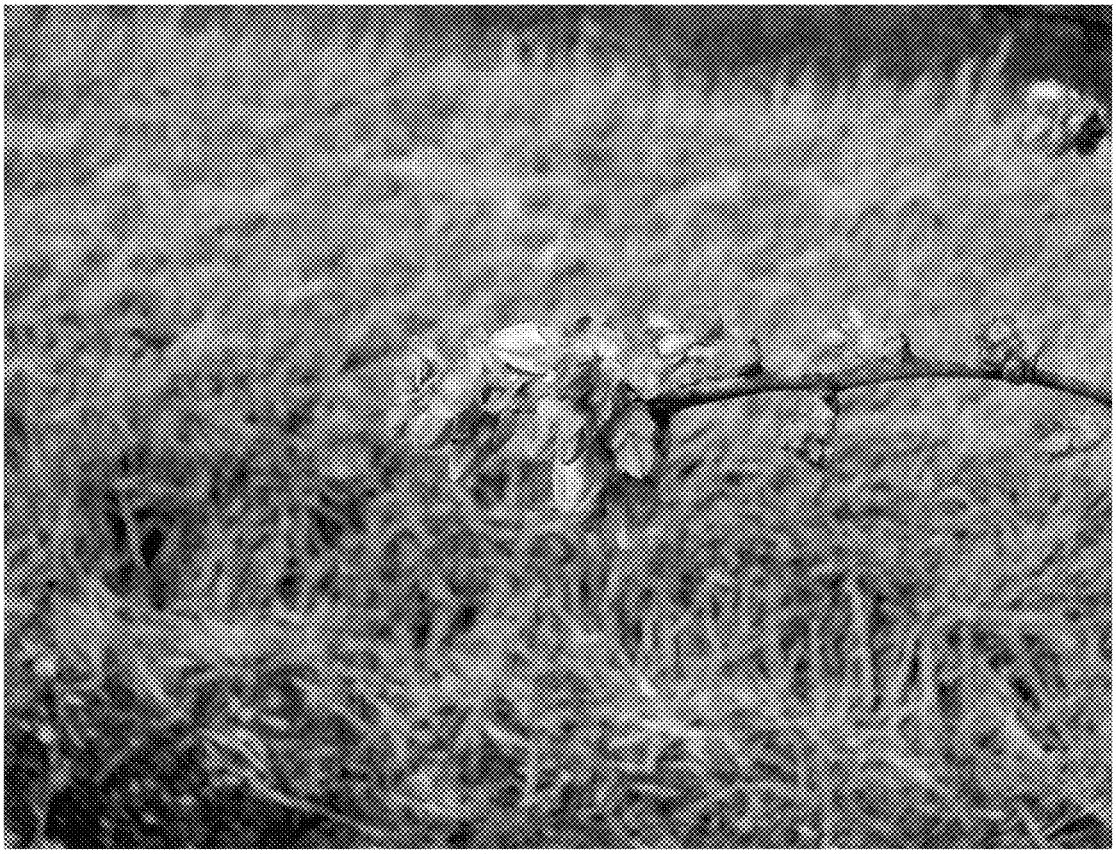
FIG. 1—depicts immature flowers of the new variety 'FC13-113' on a lateral branch of a four-years old plant.
Figure 2:
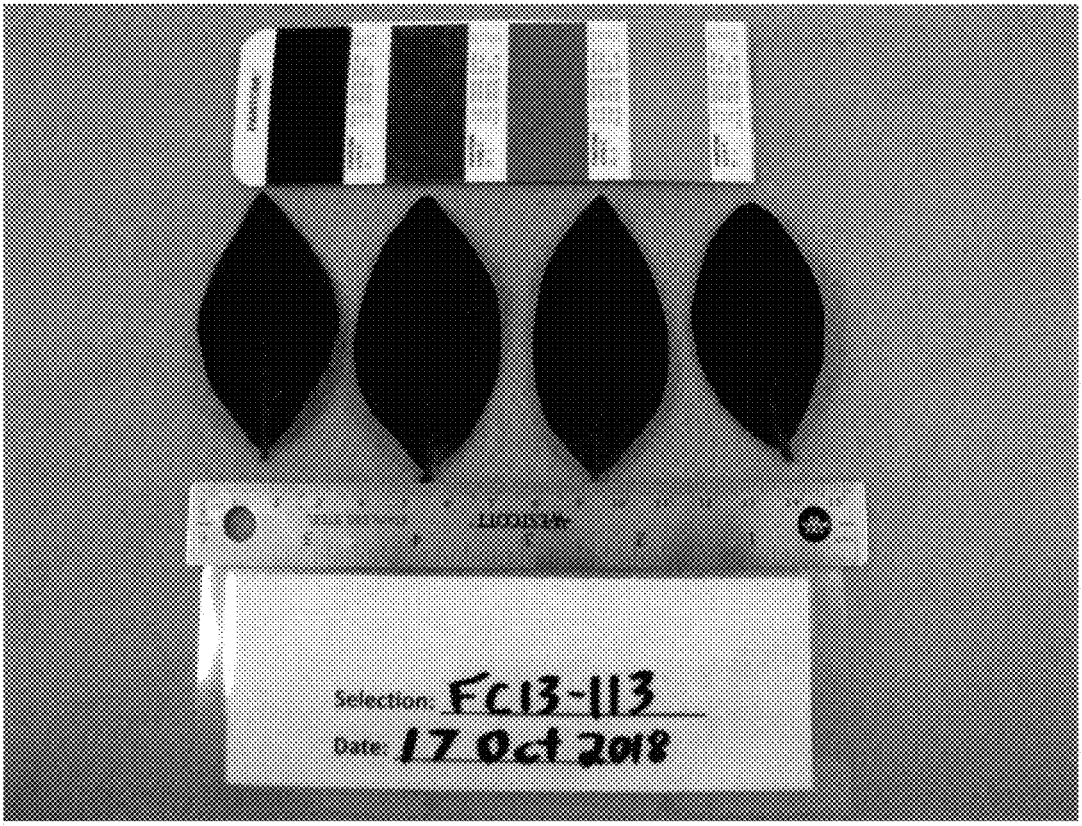
FIG. 2—depicts the fall foliage of the new variety 'FC13-113' of a four-years old plant next to the corresponding Pantone color swatch and ruler.
Figure 3:
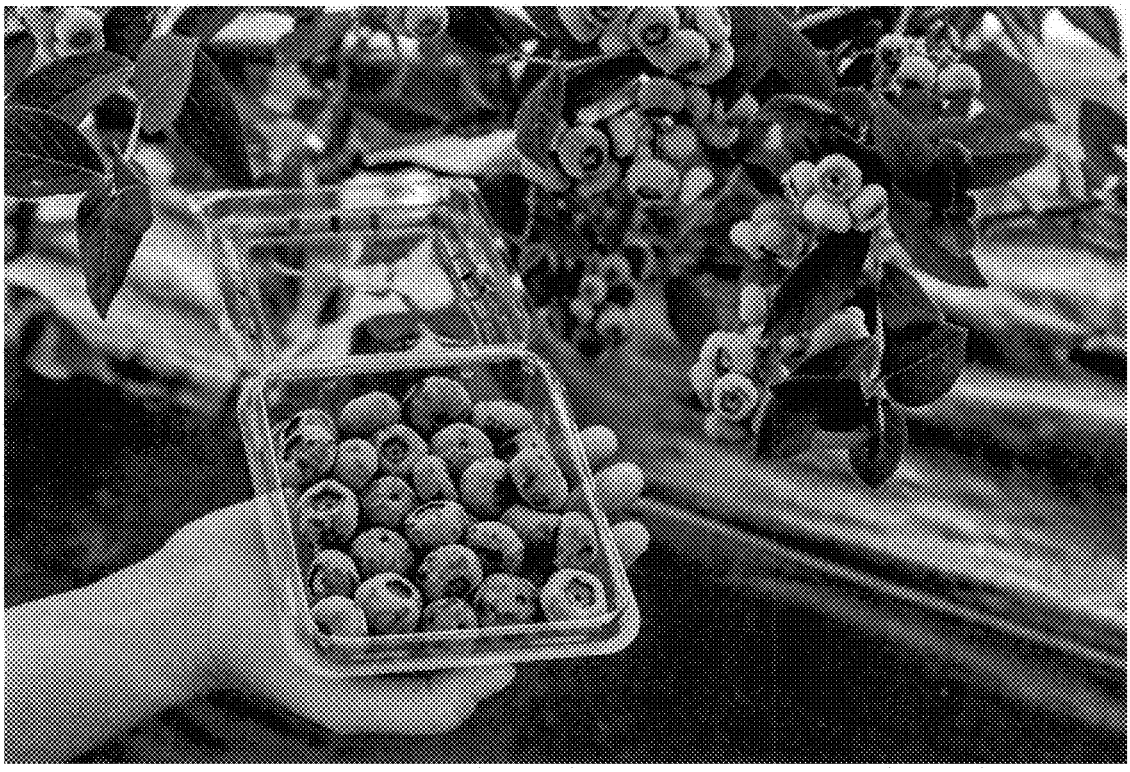
FIG. 3—depicts ripe fruit from a two-year old plant of the 'FC13-113' in a clamshell next to a mature plant of the new variety 'FC13-113', which is two-years old, in the spring.
Figure 4:
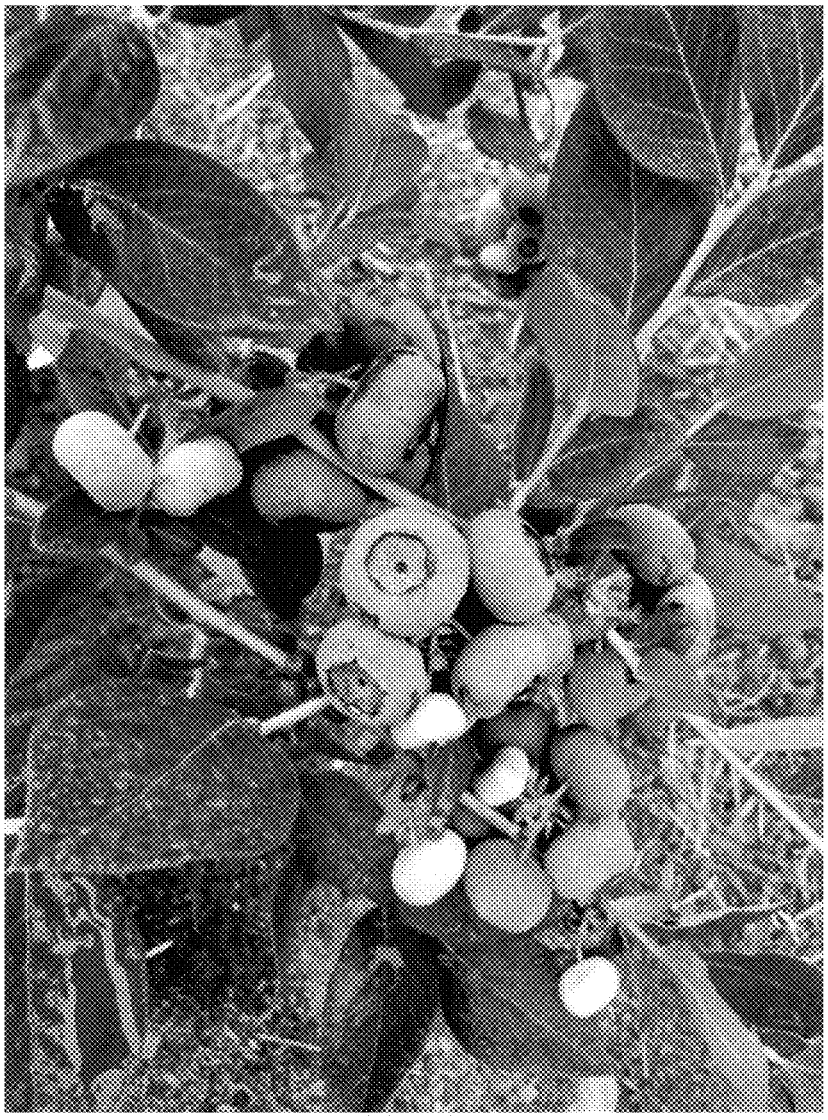
FIG. 4—depicts ripe fruit on lateral branches of the new variety 'FC13-113', which is two-years old.
Figure 5:
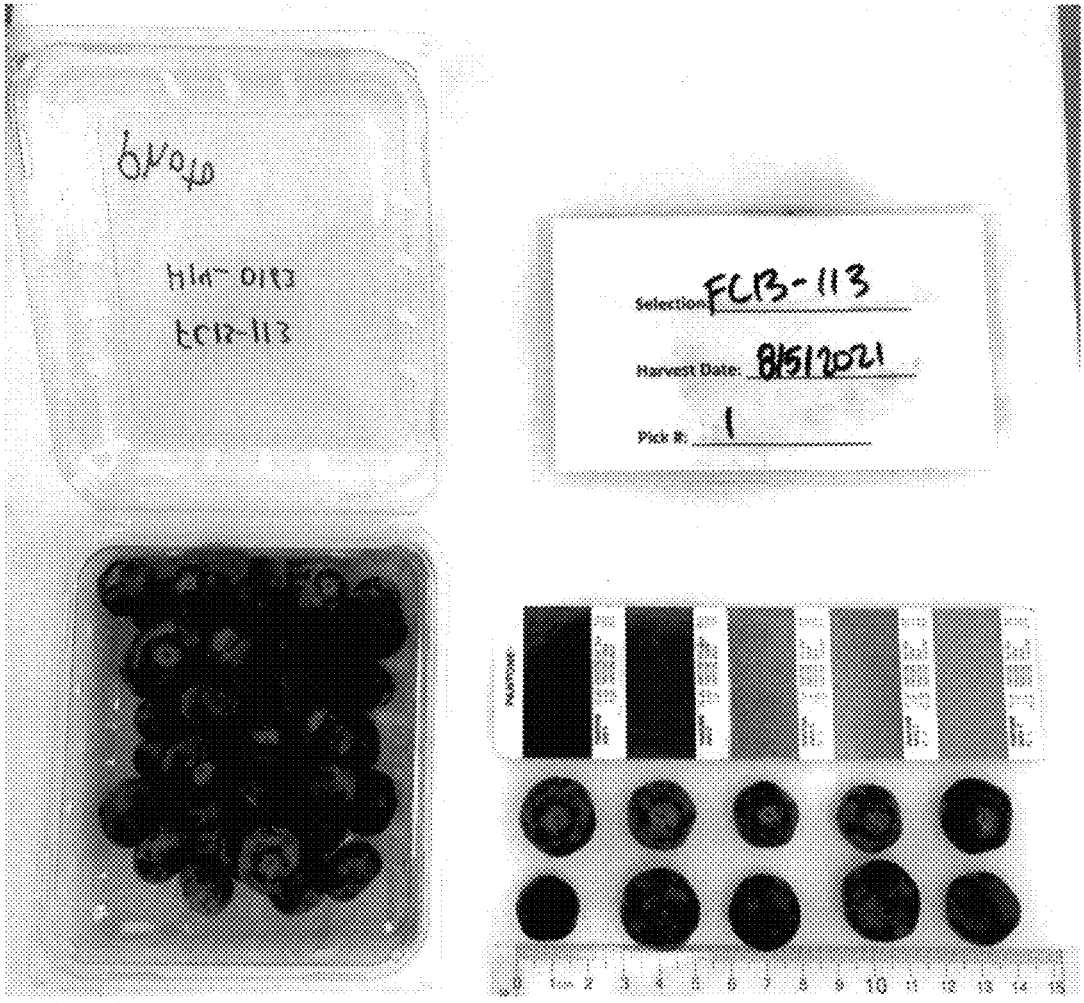
FIG. 5—depicts ripe fruit of a seven-years old plant of the new variety 'FC13-113' next to the corresponding Pantone color swatch and ruler.
Figure 6:
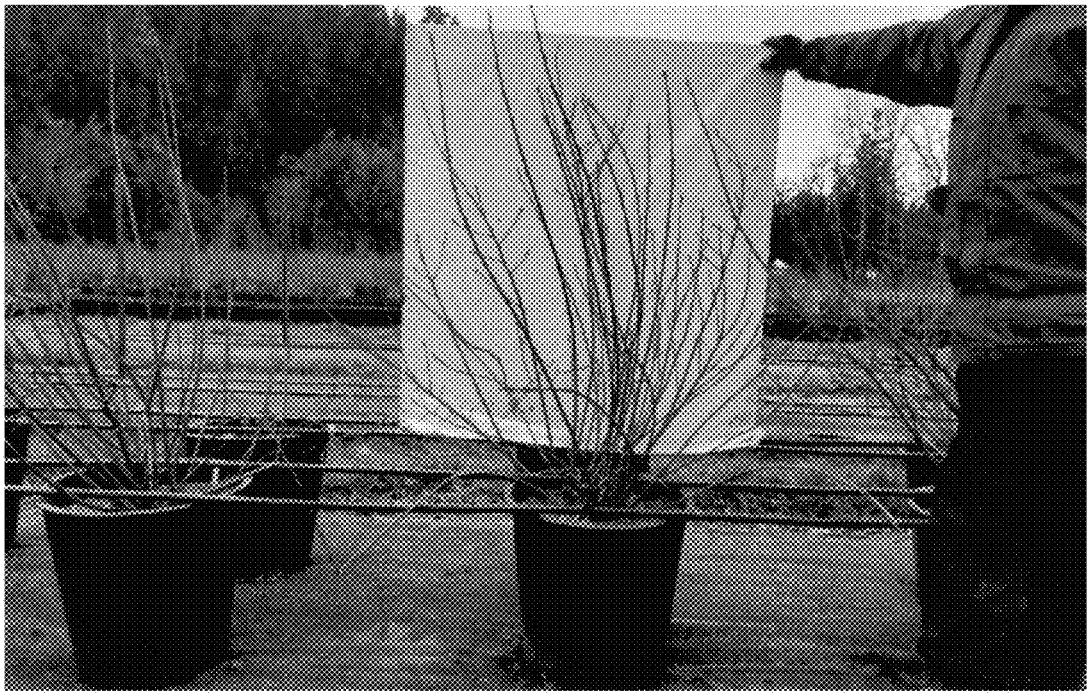
FIG. 6—depicts a mature plant of the new variety 'FC13-113', which is two-years old in the winter, against a white background.
Figure 7:
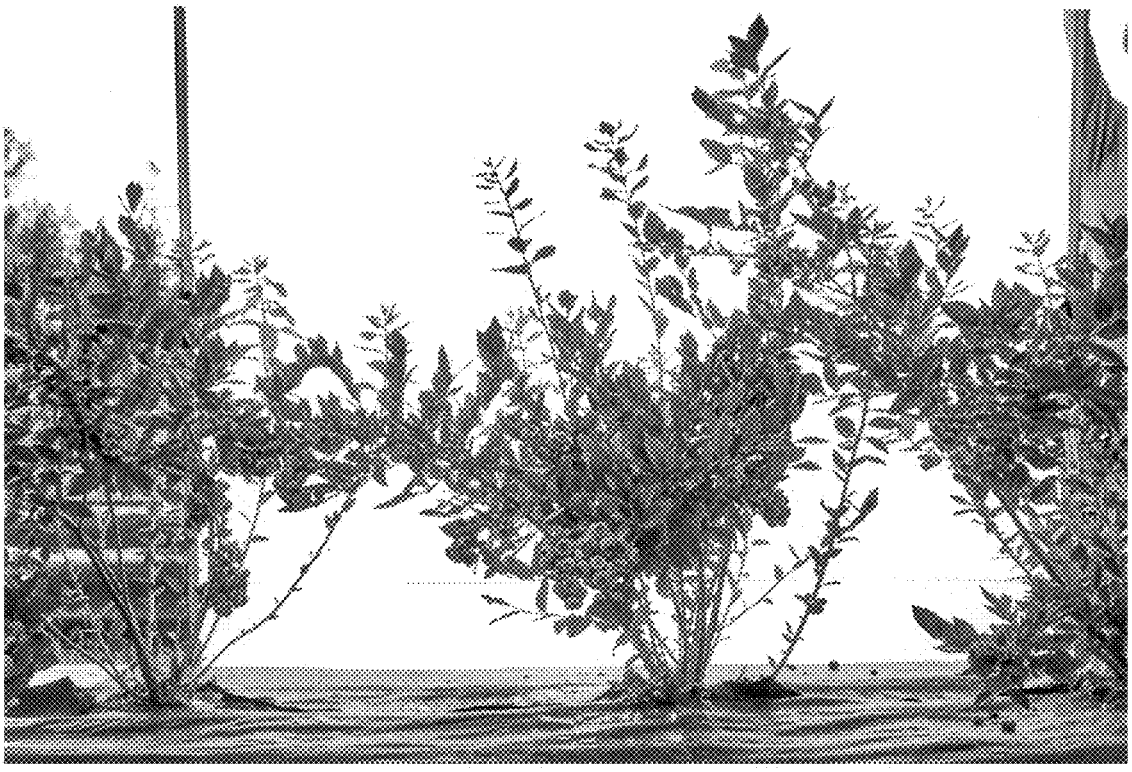
FIG. 7—depicts a mature plant of the new variety 'FC13-113', which is two-years old in the spring and displaying some ripe fruit.

The following detailed description sets forth the distinctive characteristics of 'FC13-113'. The data which defines these characteristics was collected from asexual reproductions of the original selection. Dimensions, sizes, colors, and other characteristics are approximations and averages set forth as accurately as possible. The plant history was taken on plants approximately 5 years of age, and the descriptions relate to plants grown in the field located at 39252 Jasper-Lowell Road, Lowell, Oregon, USA. Descriptions of fruit characteristics were made on fruit grown at the field described above. Color designations are from "The Pantone Book of Color" (by Leatrice Eiseman and Lawrence Herbery, Harry N. Abrams, Inc., Publishers, New York 1990) and the color designations used herein represent the closest color observed on the majority of the specified botanical feature. Where the Pantone color designations differ from the colors of the photographs, the Pantone colors are accurate.

The new blueberry plant 'FC13-113' has not been observed under all possible environmental conditions. The phenotype may vary somewhat with variations in environment and cultural practices such as temperature and light intensity without, however, any variance in genotype.

GENERAL

Classification:

*Family*.—Ericaceae.
*Genus*.—*Vaccinium*.
*Species*.—*corymbosum*.
*Common name*.—Northern Highbush Blueberry.

Parentage:

*Female parent*.—'ZF06-231' (unpatented).
*Male parent*.—'ZF08-189' (unpatented).

Market class: Hand harvest fresh market.

PLANT

General:

*Plant height*.—Average 1.26 m.
*Plant width*.—Average 1.53 m.
*Growth habit*.—Upright.
*Growth*.—Medium.
*Productivity*.—High. In Lowell, Oregon on 7-year-old plants 4.1 kilograms per plant, compared to 'Aurora' (U.S. Plant Pat. No. 15,185) plants of the same age which produced an average of 3.3 kilograms per plant; and compared to 'Liberty' (U.S. Plant Pat. No. 15,146) plants of the same age which produced an average of 3.1 kilograms per plant.
*Cold hardiness*.—Good. At trials in Central and Northwest Washington, U.S.A., where extreme low temperatures occur, no cold damage has been observed.

*Chilling requirement*.—Estimated minimum of 800-1000 hours below 45 degrees Fahrenheit.
*Leafing*.—Moderate.
*Twigginess*.—Low.
*Resistance/susceptibility to root rot* (*Phytopthora cinnamomii*).—Does not seem overly susceptible.
*Resistance/susceptibility to stem blight* (*Botryosphaeria* sp.).—Does not seem overly susceptible.
*Resistance/susceptibility to Phomopsis twig blight* (*Phomopsis vaccinii*).—Does not seem overly susceptible.
*Resistance/susceptibility to Botrytis* (*Botrytis cinerea*) .—Does not seem overly susceptible.
*Resistance/susceptibility to leaf spot* (*Septoria* spp.).—Does not seem overly susceptible.
*Resistance/susceptibility to leaf rust* (*Naohidemyces vaccinii*).—Does not seem overly susceptible.
*Resistance/susceptibility to bud mites* (*Acalatus vaccinii*).—Undetermined.

STEM

General:
*Suckering tendency*.—None.
*Mature cane color*.—Pantone color 16-1412 Stucco.
*Mature cane length*.—Average 127.25 cm.
*Mature cane width*.—Average 13.60 cm.
*Bark texture*.—Rough.
*Fruit wood color*.—Pantone color 16-1412 Stucco.
*Fruit wood length*.—Average 18.42 cm.
*Fruit wood diameter*.—Average 6.23 mm.
*Fruit wood texture*.—Smooth.
*Fall color on new shoots*.—Pantone color 19-1518 Puce.
*Surface texture of new wood*.—Smooth.
*Internode length on strong, new shoots*.—20.36 mm.
*Average number of buds per fruiting lateral*.—5.2 buds.

FOLIAGE

General:
*Time of beginning of leaf bud burst*.—On average, mid-March in Lowell, Oregon.
*Leaf color* (*top side*).—Pantone color 19-0323 Chive.
*Leaf color* (*under side*).—Pantone color 16-0213 Tea.
*Leaf arrangement*.—Alternate and spirally arranged, dextrose.
*Leaf shape*.—Broadly elliptic.
*Leaf margins*.—Entire.
*Undulation of margin*.—None.
*Leaf venation*.—Anastomosing.
*Leaf apices*.—Acute.
*Leaf bases*.—Obtuse.
*Leaf length*.—Average 62.27 mm.
*Leaf width*.—Average 32.79 mm.
*Leaf length/width ratio*.—1.90 ratio.
*Leaf nectarines*.—Absent.
*Pubescence of upper side*.—Absent.
*Pubescence of lower side*.—Absent.
*Cross sectional profile*.—Revolute.
*Longitudinal profile*.—Plane.
*Attitude*.—Porrect.
*Fall leaf color*.—Pantone color 19-1518 Puce.
Petioles:
*Length*.—Average 3.64 mm.
*Width*.—Average 1.88 mm.
*Color*.—Pantone 12-0315 White Jade.
*Petiole surface texture*.—Smooth.

FLOWERS

General:
*Time of beginning of flowering*.—Approximately mid-April in Lowell, Oregon.
*Time of* 50% *anthesis*.—Approximately early May in Lowell, Oregon.
*Flower shape*.—Urceolate.
*Flower bud density*.—Moderate.
*Flower fragrance*.—Faint and sweet.
*Immature flower color*.—Pantone color 14-1521 Peaches n' Cream.
Corolla:
*Color*.—Pantone color 11-0603 Pastel Parchment.
*Length*.—8.81 mm.
*Width*.—7.36 mm.
*Aperture width*.—3.76 mm.
*Anthocyanin coloration of corolla*.—None.
*Corolla ridges*.—Present.
*Protrusion of stigma*.—Does not protrude, level with corolla.
Inflorescence:
*Length*.—29.46 mm.
*Diameter*.—30.12 mm.
*Length of peduncle*.—19.86 mm.
*Surface texture of peduncle*.—Smooth.
*Color of peduncle*.—Pantone color 12-0626 Pale Star.
*Length of pedicel*.—6.59 mm.
*Surface texture of pedicel*.—Smooth.
*Color of pedicel*.—Pantone color 12-0626 Pale Star.
*Number of flowers per cluster*.—7.8 flowers.
*Flower cluster density*.—Medium.
Calyx (with sepals):
*Diameter*.—7.18 mm.
*Color* (*sepals*).—Pantone color 12-0426 Mellow Green.
*Texture*.—Smooth.
Stamen:
*Length*.—6.67 mm.
*Number per flower*.—10 stamen per flower.
*Filament color*.—Pantone color 12-0418 Hay.
Pistil:
*Length*.—9.02 mm.
*Ovary color* (*exterior*).—Pantone color 16-0228 Jade Green.
*Style length*.—8.72 mm.
Anther:
*Length*.—4.34 mm.
*Number*.—2 anthers per stamen.
*Color*.—Pantone color 17-1048 Inca Gold.
Pollen:
*Abundance*.—Moderate.
*Color*.—Pantone color 11-0105 Antique White.

FRUIT

General:
*Time of* 50% *maturity*.—Approximately the last week of July in Lowell, Oregon.
*Fruit development period*.—93 days from 50% bloom to 50% blue fruit.

*Mean harvest date*.—The first harvest approximately occurs in week 31, with the majority of fruit being harvested in week 32.
*Mean date last pick*.—The last harvest approximately occurs in week 35 or 36.
*Fruiting type*.—On one year shoots only.
*Cluster density*.—Medium-tight.
*Berries per cluster*.—5.2 berries.
*Unripe fruit color*.—Pantone color 13-0540 Wild Lime.
*Ripe berry color*.—Pantone color 16-3919 Purple Cloud.
*Berry skin color after polishing*.—Pantone color 19-4101 Ebony.
*Berry surface wax abundance*.—Moderate to high.
*Berry flesh color*.—Pantone color 13-0532 Celery Green.
*Berry weight*.—Average 3.35 grams.
*Berry height from calyx to scar*.—12.91 mm.
*Berry diameter*.—19.83 mm.
*Calyx aperture*.—Average 9.20 mm.
*Calyx depth*.—Average 1.35 mm.
*Pedicel length*.—Average 8.72 mm.
*Pedicel diameter*.—Average 3.65 mm.
*Pedicel surface texture*.—Smooth.
*Pedicel color*.—Pantone color 12-0626 Pale Star.
*Berry detachment force*.—Medium.
*Berry shape*.—Very oblate.
*Fruit stem scar*.—Medium, 1.90 mm.
*General flavor*.—Sweet aromatic flavor.
*Sweetness when ripe*.—High.
*Firmness when ripe*.—Very firm.
*Acidity when ripe*.—Medium.
*Storage quality*.—Excellent.

SEED

General:

*Seed abundance in fruit*.—Medium, average 65.6 seeds per fruit.
*Seed color*.—Pantone color 17-1134 Brown Sugar.
*Seed dry weight*.—0.267 mg per seed.
*Seed length*.—Average 1.5 mm.

COMPARISON BETWEEN COMMERCIAL CULTIVARS

TABLE 1

Comparison Table

| Denomination of similar variety | Characteristic for comparison | State of expression of similar variety | State of expression of candidate variety 'FC13-113' |
|---|---|---|---|
| 'Aurora' (U.S. Plant Patent No. 15,185) | Sugar: Acid Ratio | 9.35 | 13.25 |
| 'Last Call' (U.S. Plant Patent No. 25386) | Berry Diameter | 17.10 mm | 19.83 mm |
| 'Aurora' (U.S. Plant Patent No. 15,185) | Fruit Firmness (Firm Tech Fruit Firmness Tester) | 182.38 g/mm | 257.47 g/mm |
| 'Liberty' (U.S. Plant Patent No. 15,146) | % Harvest Below 16 mm Diameter Fruit Size | 77.67% | 10.87% |

The invention claimed is:

1. A new and distinct variety of blueberry plant named 'FC13-113', substantially as illustrated and described herein.

* * * * *